(12) United States Patent
Stähler et al.

(10) Patent No.: US 7,470,540 B2
(45) Date of Patent: Dec. 30, 2008

(54) METHOD AND DEVICE FOR THE INTEGRATED SYNTHESIS AND ANALYSIS OF ANALYTES ON A SUPPORT

(75) Inventors: Cord F. Stähler, Weinheim (DE); Ramon Güimil, Heidelberg (DE); Matthias Scheffler, Ladenburg (DE); Peer F. Stähler, Mannheim (DE); Anke Heidbrede, Mannheim (DE)

(73) Assignee: Febit AG, Mannheim (DE)

( * ) Notice: Subject to any disclaimer, the term of this patent is extended or adjusted under 35 U.S.C. 154(b) by 733 days.

(21) Appl. No.: 10/399,450

(22) PCT Filed: Oct. 17, 2001

(86) PCT No.: PCT/EP01/12027

§ 371 (c)(1),
(2), (4) Date: Aug. 1, 2003

(87) PCT Pub. No.: WO02/32567

PCT Pub. Date: Apr. 25, 2002

(65) Prior Publication Data

US 2004/0043509 A1  Mar. 4, 2004

(51) Int. Cl.
*G01N 33/00* (2006.01)
*B01J 19/00* (2006.01)

(52) U.S. Cl. .......................... 436/34; 422/129; 436/43; 436/52; 436/86; 436/87; 436/89; 436/104; 436/165; 436/177; 436/178; 436/524; 436/528; 436/531

(58) Field of Classification Search ............... 422/58, 422/61, 69, 81, 82.01–82.03, 82.05–82.09, 422/100–101, 129, 130–131; 436/34, 43, 436/52, 86–99, 104, 164–165, 177–178, 436/524–534
See application file for complete search history.

(56) References Cited

U.S. PATENT DOCUMENTS 5,247,180 A    9/1993   Mitcham et al.
(Continued)

FOREIGN PATENT DOCUMENTS

CA           2341894       *  3/2000
(Continued)

OTHER PUBLICATIONS

Kindervater, R. et al, Analytica Chimica Acta 1990, 234, 113-117.*
(Continued)

*Primary Examiner*—Arlen Soderquist
(74) *Attorney, Agent, or Firm*—Rothwell, Figg, Ernst & Manbeck, P.C.

(57) ABSTRACT

A method for preparing receptor-coated particles is described which comprises the following steps:
a) providing a support body,
b) conducting a liquid containing particles into or onto the support body,
c) immobilizing the particles on at least one surface area of the support body,
d) conducting a liquid which contains receptors or receptor building blocks for synthesizing polymeric receptors over the immobilized particles,
e) coupling the receptors or receptor building blocks location—or/and time-specifically to the immobilized particles at in each case predetermined positions of the support body,
f) repeating, where appropriate, the steps (d) and (e), until the desired receptors have been synthesized on the immobilized particles at the in each case predetermined positions of the support body.

6 Claims, 9 Drawing Sheets

U.S. PATENT DOCUMENTS

| | | | |
|---|---|---|---|
| 5,318,679 | A | 6/1994 | Nishioka |
| 5,405,783 | A | 4/1995 | Pirrung et al. |
| 5,424,186 | A | 6/1995 | Fodor et al. |
| 5,474,796 | A | 12/1995 | Brennan |
| 5,512,439 | A * | 4/1996 | Hornes et al. ............... 435/6 |
| 5,545,531 | A | 8/1996 | Rava et al. |
| 5,605,662 | A * | 2/1997 | Heller et al. ............ 422/68.1 |
| 5,610,287 | A * | 3/1997 | Nikiforov et al. ......... 536/24.3 |
| 5,653,939 | A | 8/1997 | Hollis et al. |
| 5,677,195 | A | 10/1997 | Winkler et al. |
| 5,723,320 | A | 3/1998 | Dehlinger |
| 5,728,251 | A | 3/1998 | Check, III |
| 5,741,411 | A | 4/1998 | Yeung et al. |
| 5,755,942 | A | 5/1998 | Zanzucchi et al. |
| 5,759,820 | A * | 6/1998 | Hornes et al. ............. 435/91.1 |
| 5,807,525 | A | 9/1998 | Allen et al. |
| 5,843,655 | A | 12/1998 | McGall |
| 5,846,708 | A | 12/1998 | Hollis et al. |
| 5,952,172 | A | 9/1999 | Meade et al. |
| 5,968,745 | A | 10/1999 | Thorp et al. |
| 6,001,311 | A | 12/1999 | Brennan |
| 6,024,925 | A | 2/2000 | Little et al. |
| 6,066,448 | A | 5/2000 | Wohlstadter et al. |
| 6,136,269 | A | 10/2000 | Winkler et al. |
| 6,251,691 | B1 * | 6/2001 | Seul ............................ 436/534 |
| 6,271,957 | B1 | 8/2001 | Quate et al. |
| 6,295,153 | B1 | 9/2001 | Garner |
| 6,375,903 | B1 | 4/2002 | Cerrina et al. |
| 6,420,169 | B1 | 7/2002 | Read et al. |
| 6,541,203 | B2 * | 4/2003 | Mitchison ...................... 435/6 |
| 6,586,211 | B1 | 7/2003 | Stähler et al. |
| 7,097,974 | B1 * | 8/2006 | Stahler et al. .................. 435/6 |
| 2002/0160427 | A1 | 10/2002 | Beier et al. |
| 2003/0068644 | A1 * | 4/2003 | Baum ........................ 435/7.1 |
| 2003/0175781 | A1 | 9/2003 | Beier |
| 2003/0198948 | A1 | 10/2003 | Stähler et al. |
| 2004/0043509 | A1 | 3/2004 | Stähler et al. |
| 2004/0175734 | A1 | 9/2004 | Stähler et al. |
| 2005/0037407 | A1 | 2/2005 | Beier et al. |

FOREIGN PATENT DOCUMENTS

| | | | |
|---|---|---|---|
| CA | 2341896 | * | 3/2000 |
| CA | 2345157 | A1 | 6/2000 |
| CA | 2371938 | A1 | 7/2000 |
| DE | 8309254.4 | U1 | 1/1985 |
| DE | 04241871 | A1 | 6/1994 |
| DE | 69012119 | T2 | 12/1994 |
| DE | 04325724 | A1 | 2/1995 |
| DE | 69217497 | T2 | 6/1997 |
| DE | 69218572 | T2 | 11/1997 |
| DE | 19731479 | A1 | 8/1998 |
| DE | 69032277 | T2 | 12/1998 |
| DE | 69130251 | T2 | 5/1999 |
| DE | 19823876 | A1 | 12/1999 |
| DE | 19940751 | A1 | 3/2000 |
| DE | 19842164 | | 4/2000 |
| DE | 19921940 | A1 | 6/2000 |
| DE | 19926457 | A1 | 7/2000 |
| DE | 69328693 | T2 | 8/2000 |
| DE | 199 10 392 | A | 9/2000 |
| DE | 19910392 | A1 | 9/2000 |
| EP | 297290 | * | 1/1989 |
| EP | 368808 | * | 5/1990 |
| EP | 0430248 | A2 | 6/1991 |
| EP | 0493137 | A1 | 7/1992 |
| EP | 0549993 | A1 | 7/1993 |
| EP | 0671626 | A1 | 9/1995 |
| EP | 0955085 | A2 | 11/1999 |
| JP | 9288080 | | 11/1997 |
| WO | 89/03533 | * | 4/1989 |
| WO | WO 91/18276 | A1 | 11/1991 |
| WO | WO 92/10092 | A1 | 6/1992 |
| WO | WO 93/20230 | A1 | 10/1993 |
| WO | WO 93/22678 | A2 | 11/1993 |
| WO | WO 95/01559 | A2 | 1/1995 |
| WO | WO 95/12808 | A1 | 5/1995 |
| WO | WO 96/10747 | A1 | 4/1996 |
| WO | WO 96/33971 | A1 | 10/1996 |
| WO | WO 96/40712 | A1 | 12/1996 |
| WO | WO 97/06468 | A2 | 2/1997 |
| WO | WO 97/12030 | A1 | 4/1997 |
| WO | WO 97/19749 | A1 | 6/1997 |
| WO | 97/40385 | * | 10/1997 |
| WO | WO 97/39151 | A1 | 10/1997 |
| WO | WO 97/41425 | A1 | 11/1997 |
| WO | WO 98/03683 | A1 | 1/1998 |
| WO | WO 98/08085 | A1 | 2/1998 |
| WO | WO 98/13683 | A1 | 4/1998 |
| WO | WO 98/30893 | A1 | 7/1998 |
| WO | WO 98/51819 | A1 | 11/1998 |
| WO | WO 98 53093 | A | 11/1998 |
| WO | WO 98/58293 | A2 | 12/1998 |
| WO | WO 99/09042 | A2 | 2/1999 |
| WO | WO 99/19510 | A1 | 4/1999 |
| WO | WO 99/27140 | A1 | 6/1999 |
| WO | WO 99/31275 | A1 | 6/1999 |
| WO | 19901761 | A1 | 7/1999 |
| WO | WO 99/37819 | A2 | 7/1999 |
| WO | WO 99/39817 | A1 | 8/1999 |
| WO | WO 99/42813 | A1 | 8/1999 |
| WO | WO 99/41007 | A2 | 9/1999 |
| WO | WO 99/60156 | A2 | 11/1999 |
| WO | WO 99 60170 | A1 | 11/1999 |
| WO | WO 99/63385 | A1 | 12/1999 |
| WO | WO 00/11473 | A1 | 3/2000 |
| WO | WO 00 13017 | A | 3/2000 |
| WO | WO 00 13018 | A | 3/2000 |
| WO | WO 02/32567 | A1 | 4/2002 |

OTHER PUBLICATIONS

Gunther, A. et al, Analytica Chimica Acta 1995, 300, 117-125.*
Mancini, A. et al, Molecular and Cellular Biochemistry 1996, 162, 83-87.*
Peter, J. et al, Analytical Chemistry 1997, 69, 2077-2079.*
Khng, H. P. et al, Biotechnology and Bioengineering 1998, 60, 419-424.*
Chaix, C. et al, Journal of Applied Polymer Science 1998, 70), 2487-2497.*
Kirner, T. et al, Biophysical Chemistry 1999, 79, 163-186.*
Beier, M. et al, Nucleic Acids Research 1999, 27, 1970-1977.*
Velev, O. D. et al, Langmuir 1999, 15, 3693-3698.*
Beier, M. et al, Nucleosides & Nucleotides 1999, 18, 1301-1304.*
Nanthakumar, A. et al, Bioconjugate Chemistry 2000, 11, 282-288.*
Penchovsky, R. et al, Nucleic Acids Research 2000, 28, e98/1-e98/6.*
Anonymous, Digital Optical Chemistry System, Dec. 20, 1999, from Internet.
Bertsch et al., "Study of the Spatial Resolution of a New 3D Microfabrication Process: The Microstereophotolithography Using a Dynamic Mask-generator Technique," J. Photochemistry Photobiology A: Chemistry 107:275-281, 1997.
Davidson, "A Microlens Direct-Write Concept for Lithography," SPIE 3048:346-355, 1997.
Hanley, et al. "Charge Transfer Devices in Analytical Instrumentation," Anal. Chem. 68:A661-A667, 1996.
Hoheisel, "Oligomer-Chip Technology," Trends Biotechnol., 15(11):465-469, 1997.
Johnson et al., EE Times, 2 pgs., "Micromirror Arrays Perform Photolithography Step," 1999.

Kirschner, et al., "Minaturisiete NIR-Diodenarry-Spektrometer," GIT Labor-Fachzeitschrift (English Title Translation: Miniaturizated NIR Diode Array Spectrometers), 402-404, 1998.

Neff, et al., "Two-Dimensional Spatial Light Modulators: A Tutorial," Proc. IEEE, 78(5):826-855, 1990.

Singh-Gasson et al., "Maskless Fabrication of Light-directed Oligonucleotide Microarrays Using a Digital Micromirror Array," Nat. Biotechnol., 17:974-978, 1999.

Villemoes et al., "A Computerized Peptide Synthesizer with Feed Back Control," Acta Chemica Scand. B 32:703-713, 1978.

von Buren et al., "Branched Oligodeoxynucleotides: Automated Synthesis and Triple Helical Hybridization Studies," Tetrahedron Lett. 51(31):8491-8506, 1995.

* cited by examiner

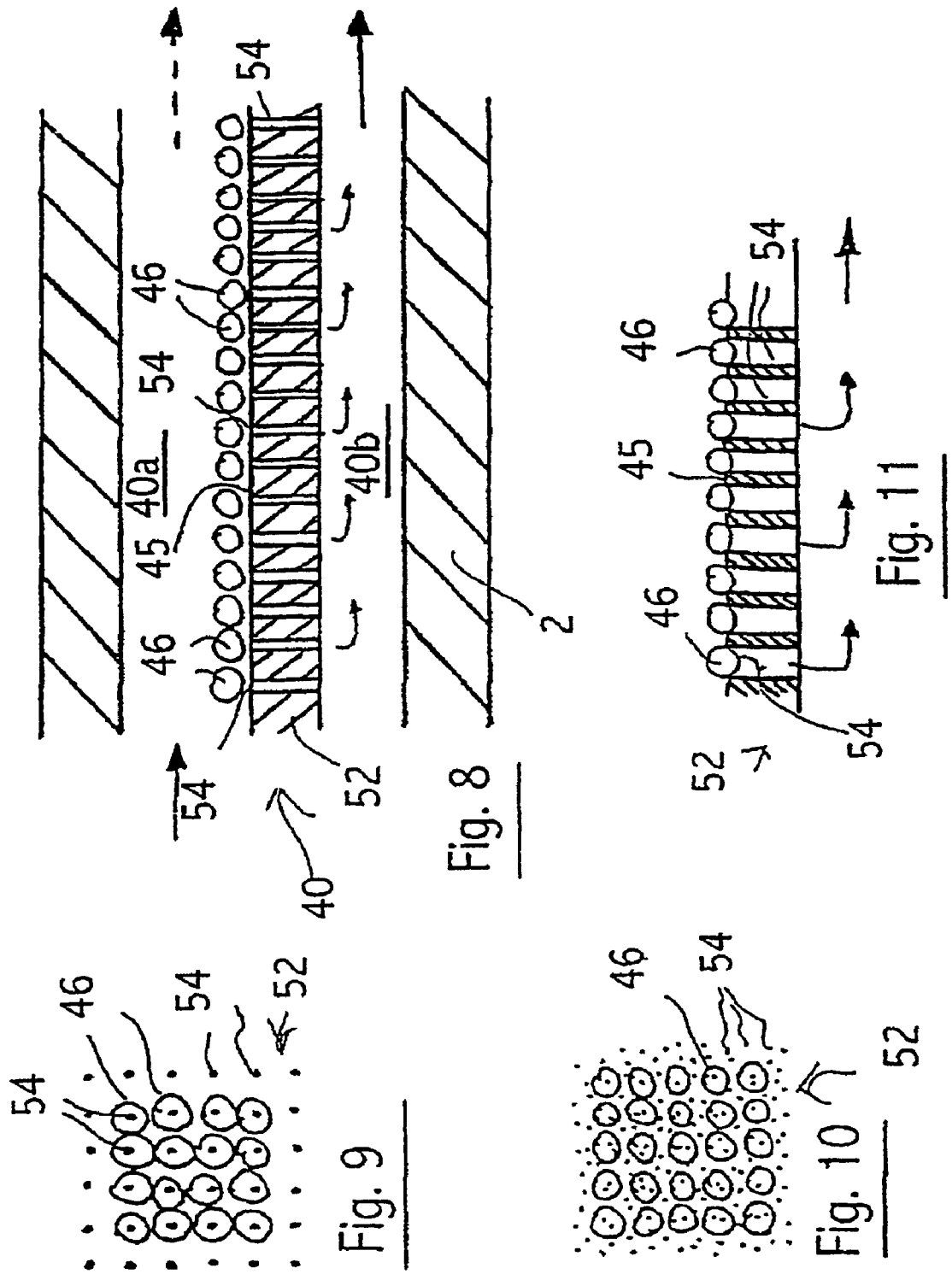

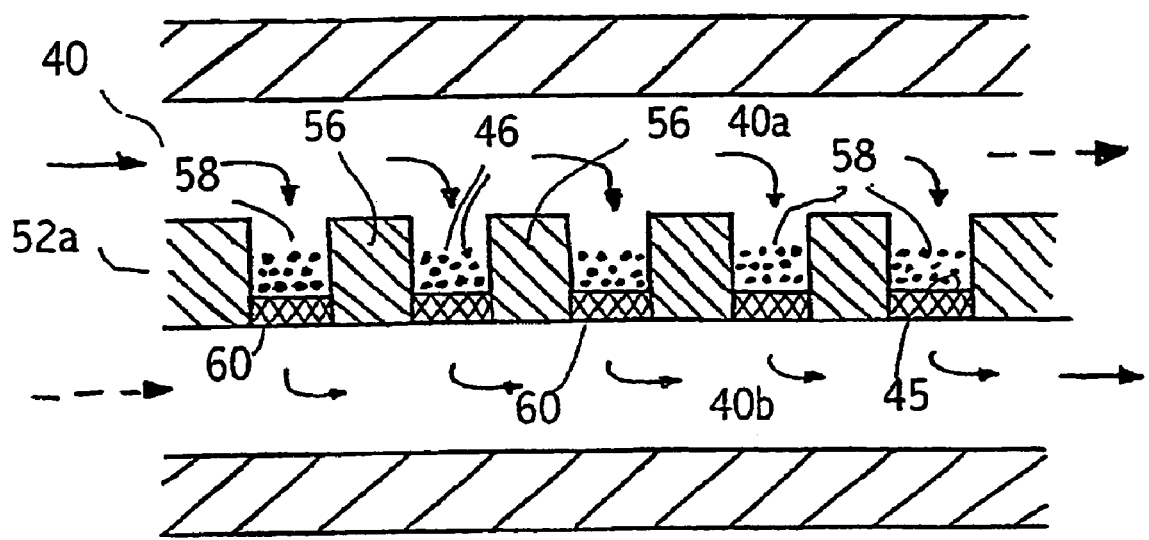
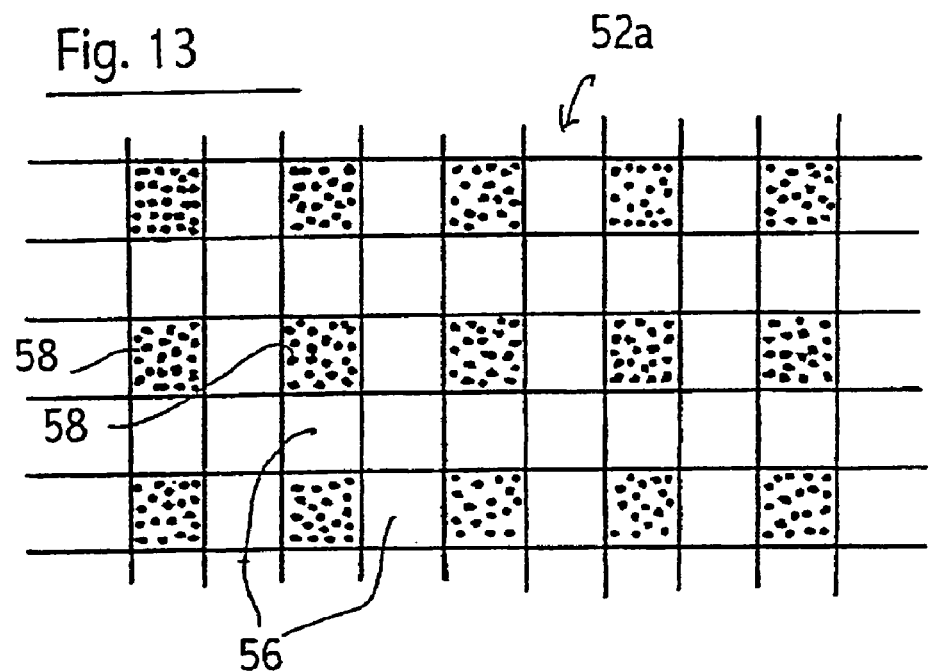
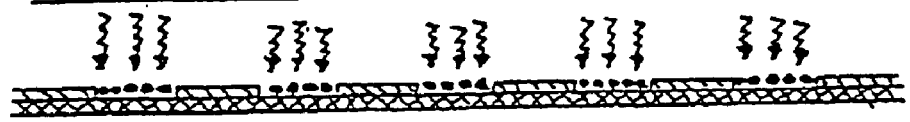

METHOD AND DEVICE FOR THE INTEGRATED SYNTHESIS AND ANALYSIS OF ANALYTES ON A SUPPORT

CROSS REFERENCE TO RELATED APPLICATION

This application is a 35 USC 371 National Phase Entry Application from PCT/EP01/12027, filed Oct. 17, 2000, and designating the U.S.

The invention relates to a method and an apparatus for integrated synthesis and analyte determination on a support.

The detection of biologically relevant information in defined investigation material is of outstanding importance for basic research in the biosciences and for medical diagnostics and for several other disciplines. The genetic information is present in the form of an enormous variety of different nucleic acid sequences, the DNA (deoxyribonucleic acid). The realization of said information usually results, via the preparation of transcripts of the DNA into RNA (ribonucleic acid), in the synthesis of proteins which for their part are frequently involved in biochemical reactions.

With respect to the technical background of the invention, reference should be made to the preparation and use of biochips. Biochips typically are miniaturized hybrid functional elements with biological and technical components, for example biomolecules immobilized on an outer surface or inner surface, which can be used as specific interaction partners. They are required for miniaturized, highly parallel analysis. The structure of said functional elements frequently has rows and columns, and in these cases the term "arrays" is used. Since thousands of biological or biochemical functional elements may be arranged on a biochip, these normally need to be manufactured using microtechnical methods. Conventional biochips usually have 2D geometry. Alternatively, the form of a biochip may also be produced by arranging two or more 1D structures (e.g. capillaries). An extension of the geometry is a 3D structure in which reactions are analyzed and, where appropriate, also manipulated or controlled in a 2D arrangement. Particularly suitable biological and biochemical functional elements are: DNA, RNA, PNA (in nucleic acids and their chemical derivatives there may be, for example, single strands, double strands, triplex structures or combinations thereof), saccharides, peptides, proteins (e.g. antibodies, antigens, receptors), derivatives produced by combinatorial chemistry (e.g. organic molecules), cellular components (e.g. organelles), cells, multicellular organisms, cell assemblages, etc.

With respect to the technical background and field of the invention presented herein, reference is made to the following patent applications and printed publications whose contents are incorporated into the present application.

DE 199 40 750 A; WO 0013018 A
DE 199 40 751 A,
DE 199 40 752 A; WO 0013017 A,
DE 199 57 116; PCT/EP00/01356,
DE 199 35 433.2; PCT/EP00/07445,
DE 199 40 810.6; WO 0012123 A.

WO 0013018 A describes supports for analyte determination methods and apparatuses and methods for the integrated synthesis and analyte determination on such supports. The supports serve as bases for a preferably light-controlled synthesis of individual bases (G, A, C and T) or of complete oligonucleotides (base sequences) to produce a highly parallel, highly planar and high-density arrangement (array) of said oligonucleotides in a solid support matrix (chip). The support contains a structure of microchannels in a flat body which is at least partially transparent. For the synthesis or immobilization of receptors, the liquid starting materials are directed through the channels in the support body and bind, locally activated, to the channel walls or to molecules already previously synthesized on the channel walls. In other words, the production of chips according to WO 0013018 A and, respectively, DE 199 40 750 A comprises the preparation of a support body which is preferably provided with microchannels and is made from a suitable transparent material and the biochemical coating process on the walls of the individual microchannels so that it is then possible to synthesize the polymeric receptors, e.g. oligonucleotides, in the channels. This involves location-specific attachment of individual receptor building blocks, oligomeric synthons (e.g. di-, tri-, tetra- or pentanucleotides) or complete base sequences (oligos) in the individual channels in the support by means of photoactivation by a suitable light source. This produces in each channel a multiplicity of receptor-equipped regions (specific binding or hybridization sites), with each region being suitable for binding and subsequent detection of a specific analyte, for example a DNA fragment, owing to its individual receptor-sequence combination. The regions are separated from one another by the channel walls in one dimension of the planar support, and an appropriate space is left between two neighboring regions along the individual channels during photoactivated binding. The result is a highly parallel, highly integrated array of specific receptors. In the system disclosed in WO 0013018 A and, respectively, DE 199 40 750 A, synthesis of the receptors and later determination of analytes is carried out by means of a light emission detection device which comprises a programmable light source matrix, a detector matrix and the support to be provided between light source matrix and detector matrix and furthermore means for feeding fluids into the support and for discharging fluids from the support. With respect to the prior art regarding the construction of light emission-light detection devices, reference is made to WO 0013017 A.

Starting from the technology mentioned above, the present invention is based on the object of providing a further improved method and an apparatus for the synthesis of a multiplicity of polymeric receptors for the purpose of forming a receptor array for the determination of analytes.

The object is achieved by proposing, in a first aspect, a method for integrated synthesis and analyte determination on a support, which comprises the following steps:
a) providing a support body,
b) conducting a liquid containing particles into or onto the support body,
c) immobilizing the particles on at least one inner or/and outer surface and/or in microstructures of the support body,
d) conducting a liquid which contains receptors or building blocks for synthesizing polymeric receptors over the immobilized particles,
e) coupling the receptors or receptor building blocks location- or/and time-specifically to the immobilized particles at in each case predetermined positions of the support body,
f) repeating, where appropriate, the steps (d) and (e), until the desired receptors have been synthesized on the immobilized particles at the in each case predetermined positions of the support body,
g) contacting the support or the synthesized receptors with a sample containing the analyte(s) to be determined, and
h) determining the analyte(s) via binding to the receptors which are coupled to the immobilized particles.

The particles are preferably "microbeads" or "microspheres" on which functionalization can take place and which may be made, for example, from ceramics, glass or plastic (e.g. also polymer gel) with or without inclusions of or combined with magnetic particles, for example. Microbeads of this kind can be obtained, for example, from Duke Scientific, Palo Alto, Calif. 94303, Dynal A. S., N-0212 Oslo, Norway. The beads can generally be produced under standard conditions and allow any kind of online or offline surface analysis for quality control.

The particles (microbeads) are intended to be used to cover relevant surface regions of the support body permanently or temporarily. Application may be carried out, for example, in a flow cell, but is particularly interesting for closed microstructures whose microchannel surfaces otherwise escape any surface analysis, thereby making quality assurance for surface functionalization more difficult.

The beads can be permanently immobilized by, for example, being covalently or noncovalently attached (e.g. bonded) to one another and/or to the surface of the support body. In production, this method is advantageous in that the surface of the support body can be generated very rapidly in a few simple process steps. The often complicated functionalization of the surface for biochemical or molecular-biological applications can be carried out beforehand in a continuous or batch process on the surface of the beads where, moreover, optimal fluidic conditions for mixing processes, etc. prevail.

The construction of a temporary reactive surface with the aid of beads in a support body is particularly interesting. Said surface may be employed in connection with in-situ methods such as, for example, in-situ synthesis and analysis of DNA/RNA, etc. In the case of the temporary bead surface, principles such as magnetic fields, electric fields or else an appropriate fluid guide in the support body can be used as holding force sources. (The beads must be magnetically or else electrically charged in an appropriate manner.) Furthermore, it is possible to utilize a chemical or physical action (e.g. reaction, diffusion, light) for fixing the particles. To this end, microstructures which represent mechanical barriers can support or make possible this effect. The size of the holding force required increases with the amount of subsequent usage of the temporarily forming surface composed of bead surfaces. A great advantage of temporary immobilization is the reduction in costs. Only the beads rather than the complete support body need to be replaced between successive process runs. The support body, for example, remains in the system as a fixed component and, accordingly, can be designed in a complex manner. This allows, for example, a multiplicity of connections (e.g. fluidically, electrically, optically) and a complex fluid guide or the integration of functional elements such as components for detection (CCD, etc.) or manipulation (microfields, microtemperature controls via CMOS circuit in the support body). Following application of the microbeads for generating a reversible surface, said microbeads may be removed again from the support body by dissolving or rinsing. The beads may then be used further, for example by conventional methods. Thus it is possible, for example, to make a substance library, generated on the beads, available in a very simple manner.

The principle features of achieving the object of the present invention relating to immobilizing the particles on the support body can be summarized as follows:

A microbead suspension is used to wet, rinse, fill or flow through the support body/support system (e.g. a flow cell, a capillary or a microchannel structure, etc.). Suitably concentrated suspensions in the spatial volume above the support body surface(s) in question provide, by utilizing gravity or electric fields (for electrically charged beads) or magnetic fields (for magnetic, in particular paramagnetic beads) or by an appropriate fluid guide in the support body (with simultaneous use of specific fluidic systems), structures which, in the ideal case, correspond to a monolayer, i.e. a single layer, and attach to one or more support body surfaces, membranes, filters, etc.

This new enlarged surface area is formed by the beads which have been coated or functionalized according to their application. According to their properties, various variants for attachment to the surface (immobilization of beads) can be distinguished in the case of mono- to polyfunctional microbeads. A fixed location during the entire process is crucial for all variants. It is possible to distinguish between temporary and permanent "bead surfaces".

Permanent "Bead Surfaces"

The preorganized structures (particles) may be attached both covalently and noncovalently by utilizing adhesive forces. In the latter case, the beads are irreversibly attached to the relevant surface or surfaces of the support body by using a solvent-resistant adhesive from the class of hot melt, contact, dispersion, reactive, polycondensation, polymerization or polyaddition adhesives (for example some epoxy adhesives). The adhesion process is based on adhesion and is composed of three components: mechanical (anchoring and intermeshing effects), physical (this includes the classical noncovalent interactions such as, for example, van der Waals-, dipole-dipole and other electrostatic forces), and chemical adhesion (this includes, in addition to chemisorption, also covalent bonds between adhesive and support body surface and/or beads).

The remaining functionality or functionalities which can be addressed selectively, partly by utilizing an orthogonal protective group concept, serve to attach molecules or molecule assemblages. In this way it is possible to synthesize on synthesis positions in the biochip (support body with immobilized beads) various biopolymers, for example peptides and oligonucleotides or biopolymers with different sequences.

Temporary "Bead Surfaces"/Permanently Covalent

Covalent attachment of the preorganized structures (particles) again distinguishes between two attachment variants: vertical linkage with the support body surface and lateral linkage between the microbeads.

Suitable for vertical anchoring on the relevant support surfaces are, inter alia, the classical coupling principles of biopolymer synthesis (e.g. peptide chemistry or phosphoramidite chemistry).

Choosing a reversible binding motif, for example the redox potential-dependent formation of a disulfide, for lateral linkage results in temporary surfaces which can be removed without trace from the support body system, after the entire process has finished.

In the case of multifunctional bead surfaces, the remaining functionalities serve to attach molecules or molecule assemblages. A suitable selection or/and utilization of an orthogonal protective group concept makes it possible to address the various functionalities selectively and to synthesize various biopolymer-bead conjugates, for example peptide and oligonucleotide or biopolymers with different sequences, on a synthesis position in the biochip.

Temporary "Bead Surfaces"/Noncovalent

Another variant is the attachment of the preorganized structures (bead particles) by pure holding forces such as gravitational forces or else electric fields (in the case of electrically charged beads) or magnetic fields (in the case of magnetic, in particular paramagnetic beads) or by an appropriate fluid guide in the support body.

In addition to microstructures which influence the fluid guide, the attachment in microstructures owing to a change in shape, size or surface due to a chemical, mechanical or physical action (e.g. reaction, diffusion, light) is also possible.

It is then, in turn, possible to couple molecules or molecule assemblages to the beads temporarily immobilized in this way. A suitable selection or/and utilization of an orthogonal protective group concept makes it possible to address the various functionalities selectively and to synthesize various biopolymer-bead conjugates, for example peptide and oligonucleotide or biopolymers with different sequences, on a synthesis position in the biochip.

After the particular process run has ended, the temporary microbead surface can be dissolved again and removed fluidically, for example by rinsing. Dissolving may be carried out, for example, by reversing or else rapidly changing the magnetic or electric holding fields or by reversing the fluidic holding flow. In the case of attachment by changing the shape, size or surface, the mobility of the particles needs to be restored, if necessary, prior to removal by rinsing.

Possible in-vitro methods are:
in-situ DNA/RNA/LNA/PNA, peptide or protein synthesis and analysis (by wet chemistry and/or photochemistry),
colored beads (magnetically or electrically attached), for example with application of luminescence,
highly parallel ECL applications (ECL array),
presynthesized beads, i.e. beads having presynthesized molecules which will be extended,
magnetic beads with electric field for optimizing hybridization (two-dimensionally or per channel or at a point/space-resolved by means of integrated circuit component),
magnetic beads with electric field and/or temperature field for optimizing hybridization,
bead-bead interactions.

A modified embodiment with initially permanently immobilized particles may provide for detaching the particles chemically from the support walls and finally removing said particles from the support by rinsing, etc.

As already mentioned, it is possible, in the case of the particularly preferred "temporary bead surface" to apply magnetic fields, electric fields, or else an appropriate fluid guide in the support body for generating an appropriate holding force for the bead particles. According to the holding principle used, the bead particles need to be magnetically or/and electrically charged or polarized. Beads may have, for example, an iron oxide core or inclusions of magnetic particles. Their surface may then be coated with silane. Microbeads of this kind are supplied, for example, as superparamagnetic particles having dimensions in the 1 µm range by Polyscience, Inc. Preference is given to using beads having average diameters of from 0.2 to 10 µm, particularly preferably from 0.4 to 5 µm.

The supports prepared with permanently immobilized beads and those prepared with temporarily immobilized beads may be used in all the fields described, for example, in WO 0013018 A or DE 199 40 750 A for supports with receptors to be synthesized directly on the support body walls.

The present invention may further provide for the bead particles to be multifunctionalized, for example bifunctionalized, for example by constructing a receptor and coupling or constructing a receptor-specific labeling group in separate synthesis steps on the immobilized bead particles.

The present invention may further provide for the bead particles to interact with one another (bead-bead interactions).

In general, the resulting field of application is the flexible and cost-effective representation and evaluation of a large number of individual and specific measuring stations in a miniaturized format, for example by miniaturized, space-resolved photochemistry and immediately following analysis. This can generate in screening methods, analytical methods and production processes a large number of method data and a large variety of products as prerequirement for dealing with and, where appropriate, reproducing the large amount of information of biological systems.

Accordingly, there is a large variety of fields of application which include:
in principle all biochip applications, in particular DNA, RNA and protein arrays,
development of compounds and testing appropriate compounds (inter alia pharmaceutical research, pharmacogenomics, etc.),
preparation or synthesis of biochemical and molecular-biological compounds,
molecular diagnostics, in-vitro diagnostics (IVD),
DNA, RNA and protein analysis (genome, transcriptome, physiome),
Screening for molecular interactions (immunology, pharmaceuticals, functional genomics),
Cytology (inter alia 2D cell analysis, similarly to FACS technique),
Molecular biology,
Histology,
Forensics.

The inventive utilization of small immobilized support particles (beads) as a basis for the synthesis of receptors entails the following improvements and advantages compared to the prior art:
minimal expenditures for the solid phase (disposable microbeads) and the support body, since the latter can be reused;
simple and cost-effective derivatization of the particle surface in batch or continuous process, since the chemical modifications can be carried out outside the complete system beforehand;
high functional integration with low running costs;
simple quality control, since standard analytical methods can be used;
first ever combination of various methods in a single system (thus it is possible, for example, due to the fixed integration of the microfluidic module (support body), to combine also more complicated electronics, for example for controlling temperature, for generating electric and/or magnetic fields or for measuring or detecting optical or electrical signals, etc., with microfluidics. Nevertheless, the costs of disposable materials remain comparatively low.
A systematic control and quality assurance of the reactive surfaces (bead surfaces) in production and furthermore the use of microfluidics in closed microstructures in the synthesis and analytical steps become possible,
The density of the beads can be determined prior to the method via measuring, for example, the intrinsic fluorescence of the beads or else of attached fluorescent markers or, where appropriate, other labels. According to a variant of the method, these labels can also be removed again, if necessary, prior to the actual method.

The invention also relates to a method for preparing receptor-coated particles for determining analytes, comprising the following steps:
a) providing a support body,
b) conducting a liquid containing particles into or onto the support body,
c) immobilizing the particles on at least one inner or/and outer surface of the support body, d) conducting a liquid which contains receptors or building blocks for synthesizing polymeric receptors over the immobilized particles, e) coupling the receptors or receptor building blocks location- or/and time-specifically to the immobilized particles at in each case predetermined positions of the support body, f) repeating, where appropriate, the steps d) and e), until the desired receptors have been synthesized on the immobilized particles at the in each case predetermined positions of the support body.

The particles provided with receptors may, for example, be removed from the support body and used later at a different site, for example in a different support body, for the determintion of analytes.

The invention also relates to a method for determining one or more analytes on a support, comprising the following steps:

a) providing a support body having at least one inner or/and outer surface, where particles with receptors coupled thereto are immobilized at in each case predetermined positions of the surface, said particles carrying different receptors in different regions, g) contacting the support body with a sample containing the analyte(s) to be determined, and h) determining the analyte(s) via binding to the receptors coupled to the immobilized particles.

The invention also relates to a method for determining one or more analytes on a support, comprising the following steps:

a) providing a support body having at least one inner or/and outer surface, where particles with receptors coupled thereto are immobilized to the surface, with a plurality of coded particle species having in each case different receptors being used and the immobilization comprising a magnetic or/and electrical interaction, g) contacting the support body or the receptors with a sample containing the analyte(s) to be determined, and h) determining the analyte(s) via binding to the receptors coupled to the immobilized particles.

The coding of the particle species may be, for example, a color coding, a size coding or/and a coding in the form of a receptor-specific labeling group on the particle surface.

The invention also relates to an apparatus for carrying out a method comprising a support body which has at least one inner or/and one outer surface region for attaching particles, in particular microbeads, whose surface has been functionalized, means for supplying the particles to the at least one surface region of the support body, a device for immobilizing the particles on the at least one surface region of the support body, means for supplying receptors or receptor building blocks A, B to particles immobilized on the at least one surface region, and means for controlling location- and/or time-specific coupling of the receptors or receptor building blocks A, B to the immobilized particles at in each case predetermined positions of the support body.

In an extended description, aspects of the invention can be outlined as follows: said invention relates to a method for in-situ preparation of permanent or temporary surfaces consisting of a multiplicity of particles (beads) of a suitable dimension (diameter in the µm or nm range) which are derivatized depending on the intended application.

In an embodiment of the method, a suitable example of a support system is a flow cell, a capillary or a microchannel structure, for example made from glasses, plates of different materials such as Si, Ge, or else plastics. Other suitable support systems may be membranes, filters, etc. The beads are preorganized on the support system.

Said preorganization may be carried out, for example, by means of gravitation, in which process structures are formed which preferably correspond to a monolayer or an ordered multilayer.

On the one hand, preorganization may be carried out by means of electric fields (in the case of electrically charged beads), in which process structures are formed which preferably correspond to a monolayer or an ordered multilayer.

Alternatively, preorganization may be carried out by means of magnetic fields (in the case of paramagnetic beads), in which process structures are formed which preferably correspond to a monolayer or an ordered multilayer.

Alternatively, preorganization may be carried out by means of an appropriate fluid guide in the support body (with simultaneous use of specific fluidic systems), whereby structures are formed which preferably correspond to a monolayer or an ordered multilayer.

Expediently, the beads are attached to one or more surface regions from a suitably concentrated suspension in the spatial volume above said surface region(s) of the support body.

The temporary surface of the preorganized beads is attached by means of holding forces such as gravitational forces or else electric fields (in the case of electrically charged beads) or magnetic fields (in the case of magnetic beads) or by an appropriate fluid guide in the support body, and made accessible to the intended application.

In another embodiment, the preorganized beads can be used together in a lateral covalent manner and be attached in the support so as to be made accessible to the intended application.

Depending on the binding motif, a temporary or permanent surface is obtained.

A temporarily fixed surface is obtained by using a reversible binding motif (e.g. redox active thiol chemistry).

In a further embodiment, the preorganized beads are linked to the support body surface in a vertical and covalent manner and attached in the support body so as to be made accessible to the intended application.

Suitable for vertical anchoring on the support body surfaces are, inter alia, the classical coupling principles of biopolymer synthesis (e.g. peptide or phosphoramidite chemistry).

In another embodiment, the preorganized beads are bonded to the support body surfaces by adhesion and attached in the support body so as to be made accessible to the intended application.

Classes of adhesives suitable for bonding are the following: melt, contact, dispersion, reactive, polycondensation, polymerization or polyaddition adhesives. A solvent-stable epoxy-based polyaddition adhesive is particularly suitable for bonding.

The remaining functionalities are used for attaching the molecules or molecule assemblages in question.

The multifunctional bead surfaces are preferably used for attaching various species so that it is possible to synthesize various biopolymer-bead conjugates, for example peptide or oligonucleotides or biopolymers with different sequences, on a single synthesis position in the biochip (support body with immobilized beads). This may be carried out by utilizing an orthogonal protective group concept in which the various functionalities address themselves selectively.

The invention is suitable for preparing or analyzing substance libraries. Components of the sample can be extracted via specific binding events by conducting a sample over the support with the immobilized beads. In this connection, it is possible to investigate in particular interactions between biomolecules such as proteins or peptides and the beads, so that the invention is also suitable for the field of proteomanalysis (proteomics).

The invention is illustrated in more detail below on the basis of the figures in which FIG. 1 shows an apparatus according to the invention in a block diagram.

FIG. 4b shows a magnified section of FIG. 4a.

FIG. 8 shows in a section of a longitudinal section diagram a fluidic channel of the support, which contains a pore wall for immobilizing bead particles.

FIG. 9 shows a section of a top view of the pore wall of FIG. 8.

FIG. 10 shows a section of a top view of a pore wall with pores more densely distributed than in FIG. 9, with the pores in FIG. 10 being distributed more or less randomly.

FIG. 11 shows another example of a wall provided with pores.

FIG. 12 shows a section of a longitudinal section diagram of a fluidic channel of the support body, which has a porous intermediate wall which forms an array of columns and depressions.

FIG. 13 shows a section of a top view of the intermediate wall of FIG. 12.

FIG. 14 shows in a section of a longitudinal section diagram a variant of an intermediate wall with porous regions of the type depicted in FIG. 12.

Figure 15:
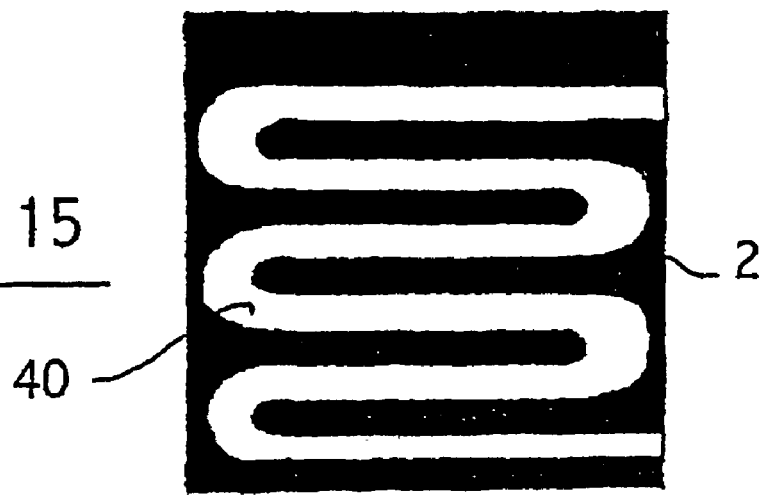
Figure 16:
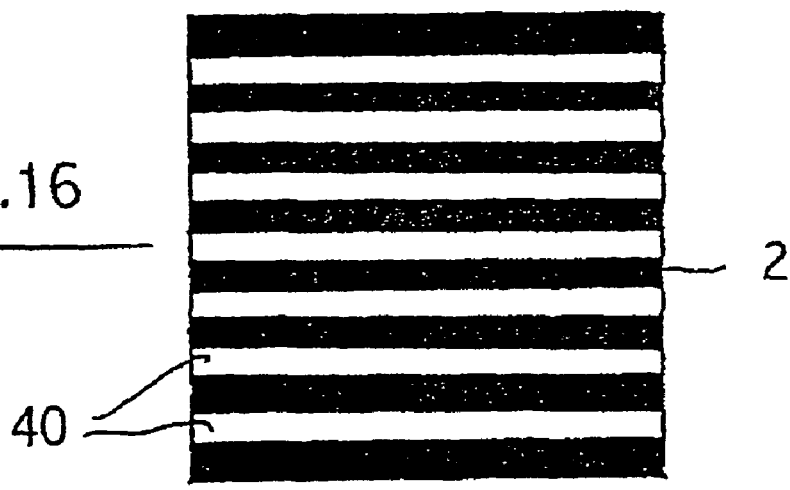
Figure 17:
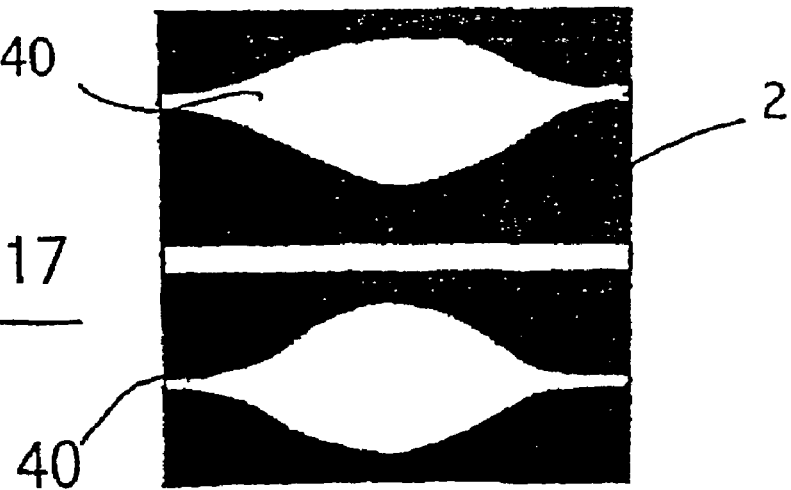

The FIGS. 15-17 show highly magnified sections and top view diagrams of the shapes and courses of various variants of microchannels in a support body.

Figure 1:
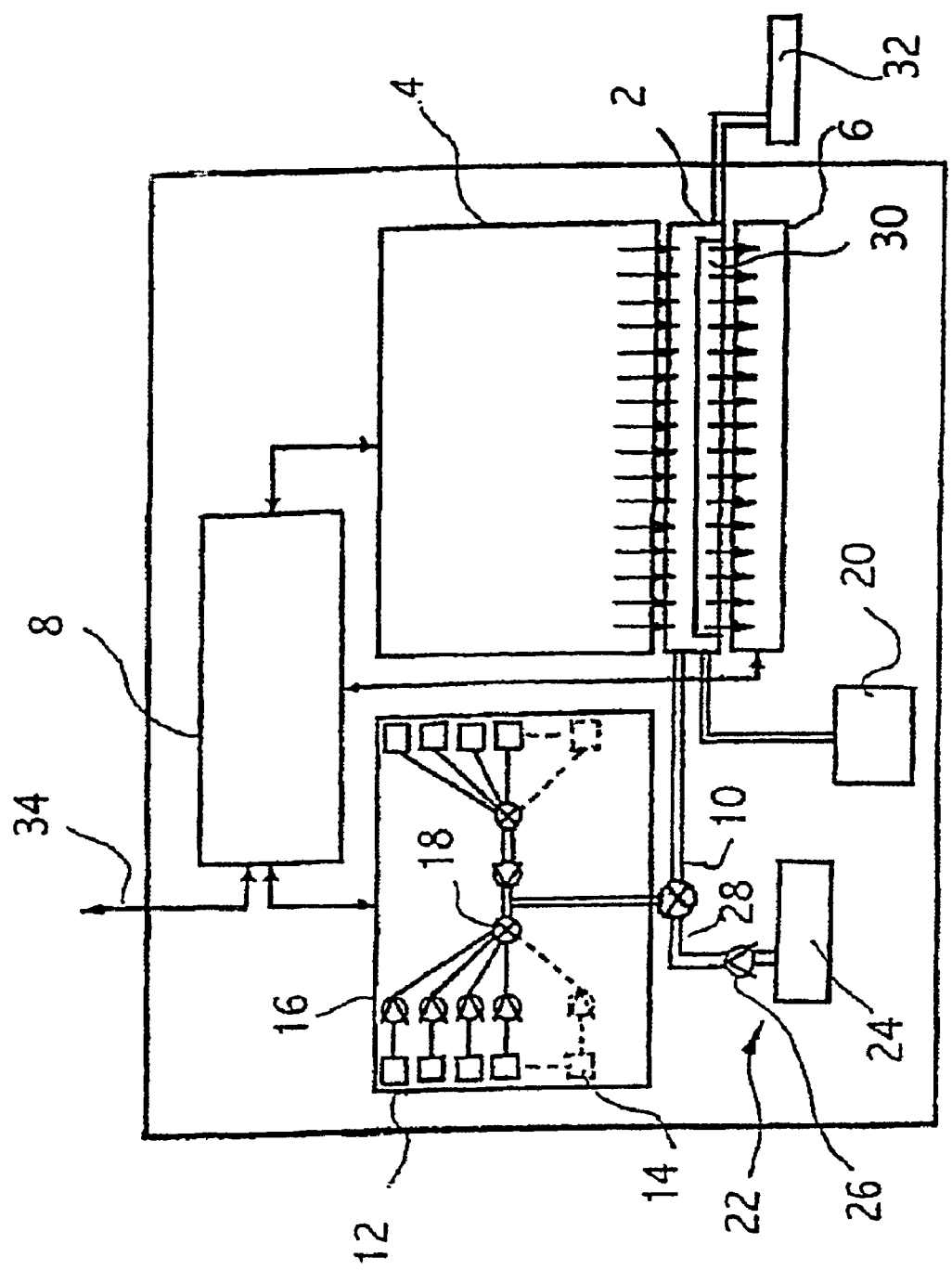

FIG. 1 shows a block diagram of an inventive apparatus for a light-assisted, integrated synthesis and, where appropriate, analytical method. The apparatus comprises a support body 2 which is pervaded by channels for transporting fluids which are not visible in FIG. 1. The support body 2 may be designed in a manner as described, for example, in WO 0013018A or in German patent application DE 199 35 433.2 and the corresponding international patent application PCT/EP00/07445. In this regard, the disclosure content thereof is incorporated into the present application.

The support body 2 is located between an illumination matrix 4 which can be controlled in a programmable manner in order to generate particular illumination patterns, and a light detector matrix 6. The support body 2 is transparent for light of the illumination matrix 6.

The illumination matrix may be, for example, a light source matrix which comprises a two dimensional array of light-emitting diodes, in particular UV diodes, or of laser elements, in particular UV laser elements. Another suitable illumination matrix is a matrix of controllable reflection elements, in which case an additional light source is required. Another suitable illumination matrix is a light valve matrix, for example an LCD matrix. WO 0013017 and DE 199 40 752 A describe in more detail the possibilities of producing an illumination matrix which are also preferred in connection with the present invention.

The programmability of the illumination matrix 4 is integrated into the system component 8 which comprises a control computer which sends appropriate control signals to the illumination matrix 4. The illumination matrix 4 illuminates the transparent support 2 according to the particular illumination pattern predetermined in the actual illumination step by the control computer 8. The fluids provided by the fluidic module 12 are transported via a fluidic connection system 10 into the support body 2 and pass through the microchannel structure thereof which is not depicted in the drawing to the reaction areas for receptor synthesis.

The light entering the support body 2 may be utilized, where appropriate, for absorption measurements, for activating photoreactions or/and for exciting fluorescence. The light exiting the support body 2 may be, for example, the light of the illumination matrix 4, which passes through the support body 2 in transmissive mode. However, it may also be light signals which are generated in the individual reaction areas in the support body 2 by fluorescence or luminescence, for example. In FIG. 1, the detector matrix 6 which comprises, for example, a CCD chip with or without intermediate optical elements is arranged opposite the illumination matrix 4, with the support body 2 located in between, in such a way that the result is a triple matrix arrangement of illumination matrix, support matrix and detector matrix. The fluidic module 12 serves to supply reaction areas in the support body 2 with, for example, starting materials, protective gases, chemicals such as solvents, etc., and sample material. The fluidic module 12 comprises tanks 14 which are emptied in a suitable manner by means of pumps 16 and valves 18. The tanks 14 may be replaced or refilled individually or as cluster. Permanently required fluids such as, for example, protective gas may also be fed by means of lines from reservoirs located outside. The fluidic waste from the various method steps can be corrected in a waste system 20.

The apparatus further comprises means 22 for supplying surface-functionalized particles, preferably microbeads, to the support body 2. The means 22 comprise a reservoir 24 for producing a particle suspension (microbead suspension) and a pump 26 for transporting the suspension from the reservoir 24 into the channel system of the support body 2. The support body 2 is connected via a line 28 with the pump 26. The means 22 for supplying surface-functionalized particles to the support body 2 may alternatively be integrated into the fluidic module 12.

A device for temporarily immobilizing the particles fed from the reservoir 24 on surfaces of the fluidic channels of the support body 2 is indicated only in a general diagrammatic form in FIG. 1 at 30.

In FIG. 1, 32 denotes a collection system for particles with receptors synthesized to the surface.

The control computer 8 takes over the control or regulation of the system. This includes, on the basis of calculating the probe or receptor sequences for the individual reaction areas, control of the illumination matrix 4 and of the fluidic module 12. It also includes control of the device 30 for temporarily immobilizing the particles (microbeads) on the fluidic channel surfaces in the support body 2. The control computer 8 further collects the data from the detector matrix 6 in order to analyze this data or, where appropriate, to forward them for analysis via an interface 34 to systems to be connected thereto.

The inventive method for integrated synthesis and analyte determination on the support 2 is carried out by activating, in a first step, the pump 26 to transport the microbead suspension from the reservoir 24 into the channel system of the support body 2. The control computer 8 activates the device 30, as a result of which microbeads are deposited from the suspension on fluidic channel areas of the support body 2 and remain there. The process may be monitored optically by means of the detector matrix 6.

After immobilizing a layer of microbeads in the support body 2 and after flushing out the remaining suspension no longer required for the further process, the receptor synthesis steps can be carried out. To this end, the control computer 8 addresses the illumination matrix 4 according to a program for generating the illumination pattern in question. At the illuminated sites, photolabile protective groups are removed from the microbeads. It is then possible for receptor building blocks to couple to these deprotected sites, which are supplied by a fluid from the fluidic module 12 and which themselves carry photolabile protective groups which can be removed in a next or later synthesis process step by illumination so that a next synthesis building block can couple to the relevant deprotected sites. In this respect, WO 0013018 A and DE 199 40 750 A describe the light-controlled synthesis of receptors (but directly on areas of the support body).

After the desired receptors have been synthesized on the immobilized microbeads at the in each case predetermined positions of the support body 2, the analyte determination step can be carried out in which the receptors are contacted with a sample containing the analyte or analytes to be determined, and the analyte or analytes are then determined via binding to the receptors, i.e. via detection of the binding to particular receptors.

Figure 2A:
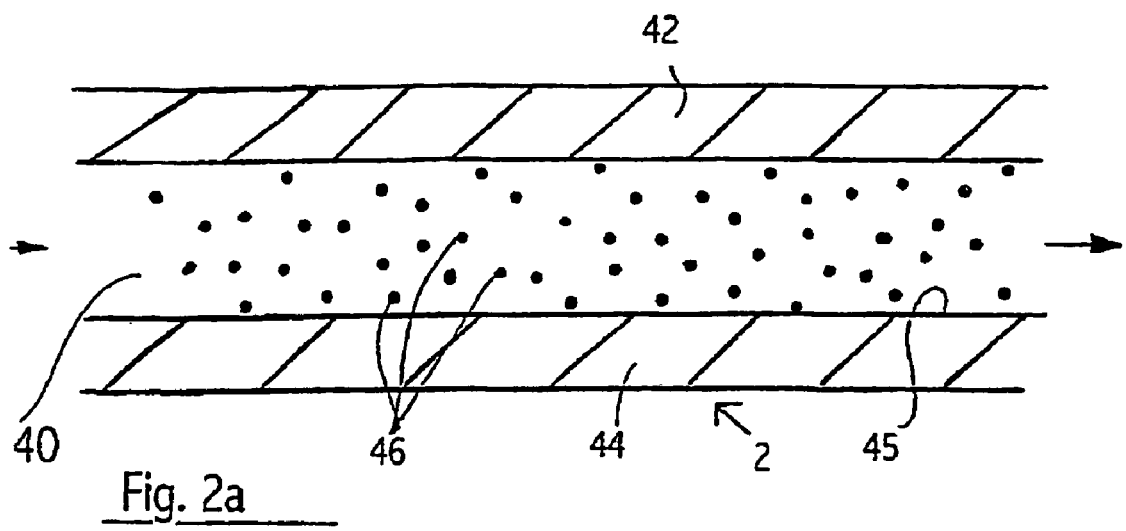
FIGS. 2a and 2b show sections of longitudinal section diagrams of a microchannel with bead particles located therein in the nonimmobilized state (FIG. 2a) and in the immobilized state (FIG. 2b).

The device 30 for immobilizing the microbeads preferably comprises means for generating a magnetic field (B field) perpendicular to the direction of flow in the fluidic channels of the support body 2. In this case, the microbeads are magnetically prepared. This can be used to produce the situation of immobilizing the microbeads 46, to be explained on the basis of the FIGS. 2a and 2b. FIG. 2a shows a section of a longitudinal section of a fluidic channel (microchannel) 40 of a support body 2 having a transparent top layer 42 and a preferably likewise transparent bottom 44. According to the diagram of FIG. 2a, a microbead suspension containing magnetic microbeads 46 flows through the channel 40.

Figure 2B:
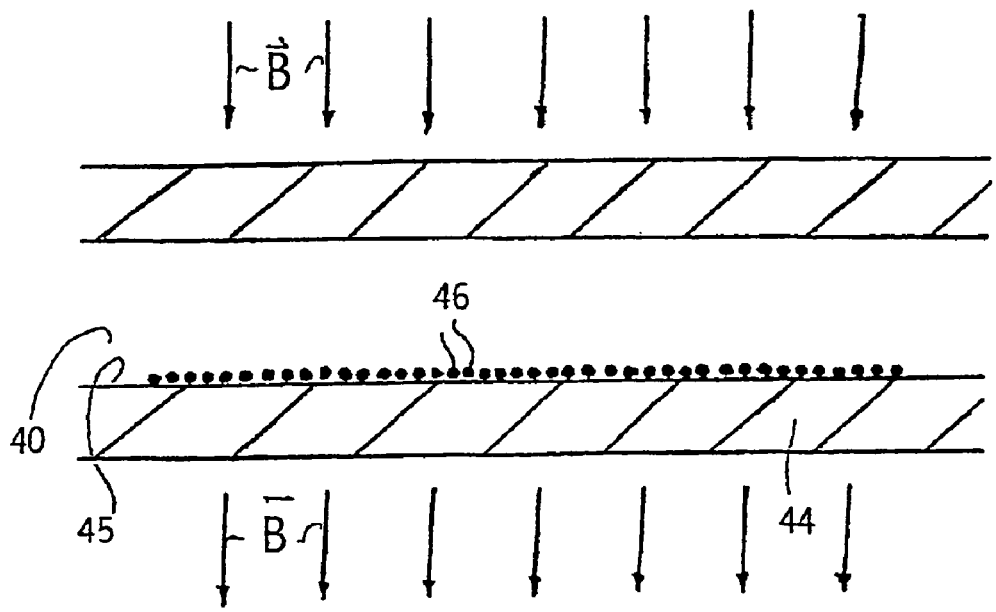

Switching on the B field leads to the situation according to FIG. 2b in which the beads 46 have been arrested and thus immobilized on the inner surface of the microchannel 40, owing to their magnetic interaction with the B field. The B field can be generated by using permanent magnets or/and electromagnetic coils.

The situation according to FIG. 2b can also be produced by using electrically charged or electrically polarized microbeads and generating in the fluidic channels 40 of the relevant support body 2 an electric field perpendicular to the direction of flow, in order to immobilize said microbeads. In this connection it may be provided for an extended electric field to be generated across the area of the support body. Alternatively, it may also be provided for electric fields to be generated at points and space-resolved with respect to particular reaction areas, for example by means of electronic elements integrated into the support body, such as, for example, CMOS transistors or, where appropriate, transparent electrodes as used in liquid crystal displays.

Figure 3A:
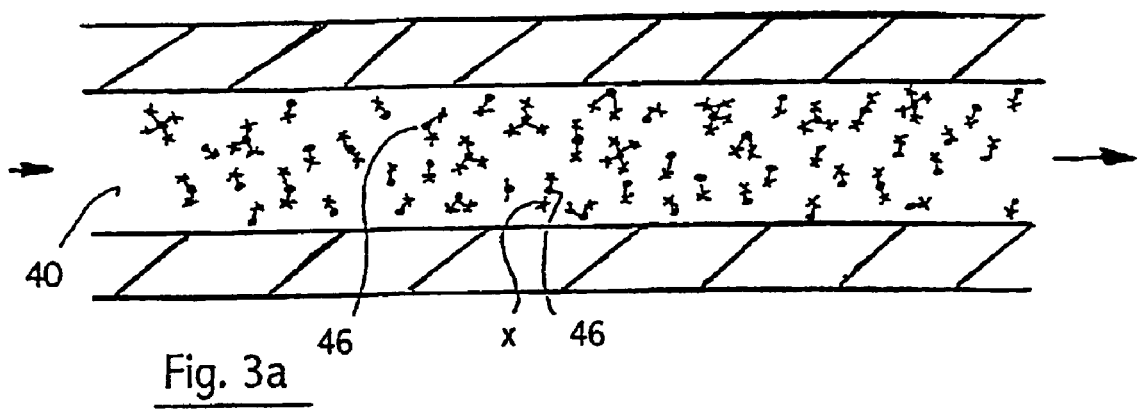
FIGS. 3a-3c show in sections of longitudinal section diagrams according to the perspective in FIGS. 2a and 2b a fluidic channel of the support body during three different steps of carrying out a synthesis method.

FIG. 3a shows, in a diagram corresponding to FIG. 2a, the microchannel 40 through which magnetic microbeads having photolabile protective groups x flow in a suspension in question.

Figure 3B:
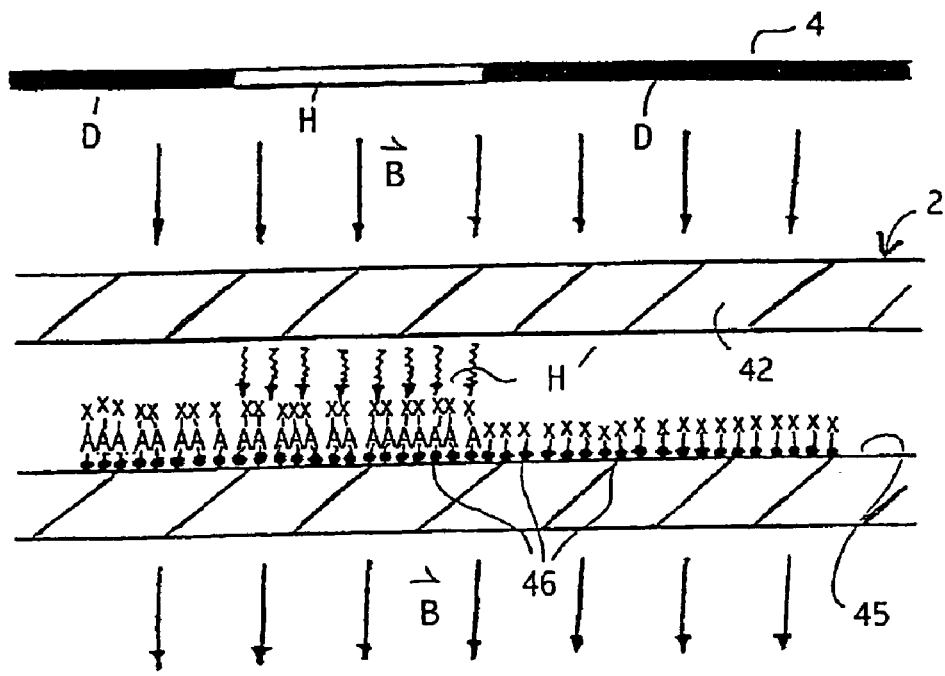
Figure 3C:
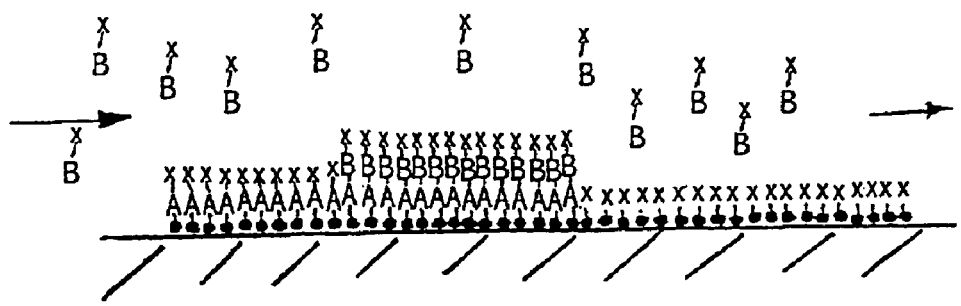

FIG. 3b illustrates a synthesis step, after magnetic microbeads 46 have been immobilized in a, in the case of the example, monolayer arranged in a planar fashion by switching on the B field and after, in a previous synthesis step, some microbeads already have a covalently attached synthesis building block A with photolabile protective group x. In FIG. 3b, 4 indicates the illumination matrix which, in the actual illumination step observed, illuminates the support body 2 through the transparent top layer 42 thereof below the position H, whereas at that moment no light is emitted or, where appropriate, reflected from the sides D of the illumination matrix 4 in the direction of the support body 2, so that a "dark field" is present below D. In the illuminated region, the radiation of the "bright field" H results in the removal of the photolabile protective groups x so that further synthetic building blocks B with photolabile protective groups x can couple to the thus deprotected microbeads 46 or synthesis building blocks A, as FIG. 3c indicates. The illumination steps with programmed controlled selection of the particular illumination pattern and the fluidic supply of relevant synthesis building blocks with photolabile protective groups are repeated, until the desired receptors have been synthesized on the immobilized particles 46 at the in each case predetermined positions of the support body 2.

Figure 4A:
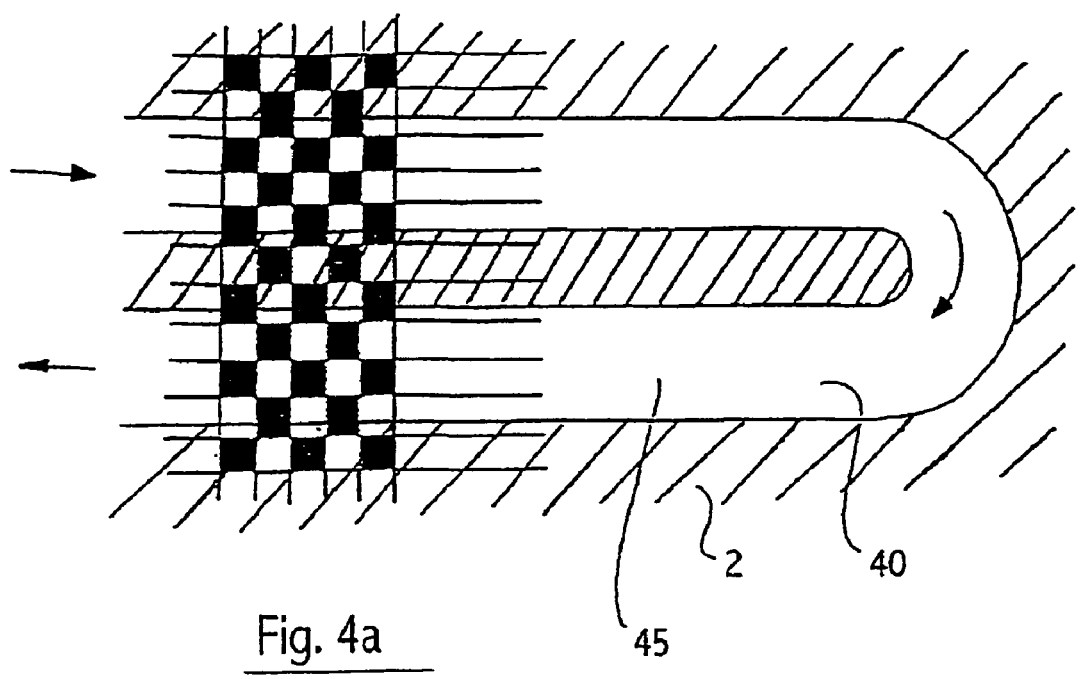
FIG. 4a shows a top view of a section through a fluidic channel of the support body, into which the drawing of an illumination pattern of an illumination matrix, projected onto the cross section, has been added.

FIG. 4a shows in a sectional top view of a section through the support body 2 a fluidic channel (microchannel) 40 and a section of a checkered patternlike bright/dark field as can be generated by the illumination matrix 4.

Figure 4B:
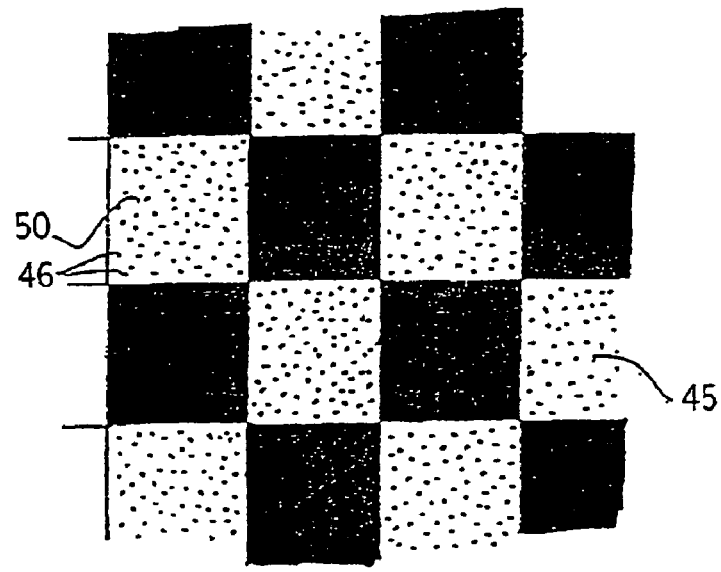

FIG. 4b shows an enlarged section of FIG. 4a, namely a region of the fluidic channel base with the bright/dark field projected thereupon. This illustrates that a relatively large number of immobilized microbeads 46 can be provided for in a particular illumination field element. The occupation density can be varied for example via the concentration of the microbeads 46 in the original microbead suspension or by choosing the time accordingly in which the microbead suspension flows through the fluidic channels 40 with the magnetic field (or electric field, where appropriate) switched on. As already mentioned, coating of the channels 40 with immobilized beads 46 can be carried out over a large area, for example by means of an appropriate B field or, where appropriate, electric field. Alternatively, it may also be possible to carry out the coating in a space-resolved manner, for example by means of space-resolved local electric fields, B fields, or, where appropriate, also by means of optical traps (similar to "laser tweezers").

With respect to FIGS. 4a and 4b, it should be noted that it is possible to generate for a subsequent illumination step a different illumination pattern than the checkered pattern shown.

Figure 5:
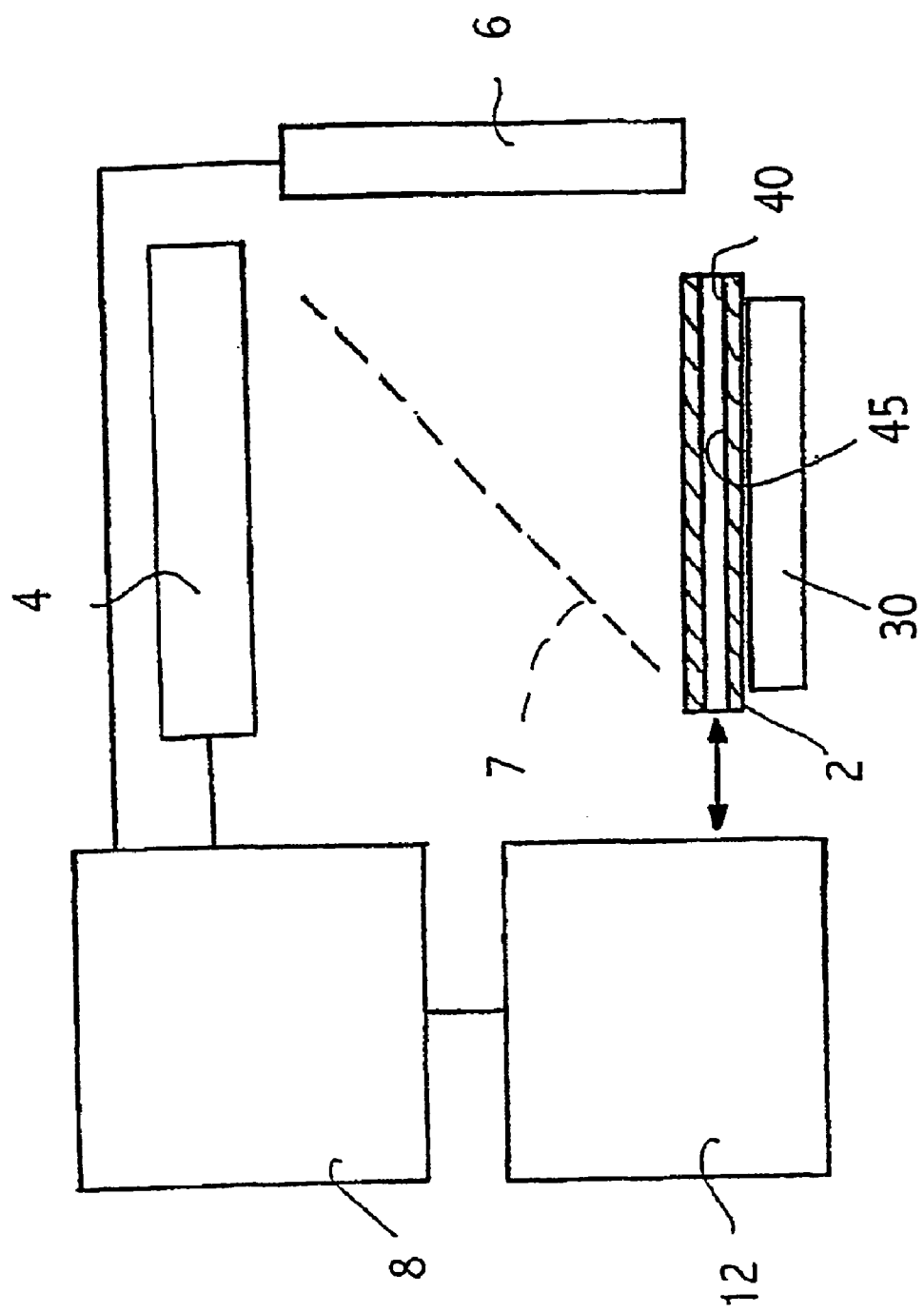
FIG. 5 shows in a block diagram a variant of the apparatus according to the invention.

FIG. 5 shows a block diagram of an inventive apparatus for reflective light observation. According to the reference numerals in FIG. 1, the apparatus comprises a control computer 8, an illumination matrix 4, a detection matrix 6, a fluid handling system (fluidic module) 12 for supplying the bead suspension to the support body 2 and for supplying the chemicals required for receptor synthesis. The device 30 provided for immobilizing the microbeads on the support body 2 is a magnetic apparatus on the side of the support body 2 facing away from the illumination matrix 4, which can, where appropriate, optionally be removed from the position shown. The device 30 may contain magnetic coils or/and permanent magnets. In FIG. 5, 7 indicates an optical beam splitter through which light of the illumination matrix 4 can pass in the direction of the support body 2. The beam splitter 7 reflects light coming from the support body 2 to the detection matrix 6. If necessary, the beam splitter 7 can be moved out of the beam path between illumination matrix 4 and support body 2.

Figure 6:
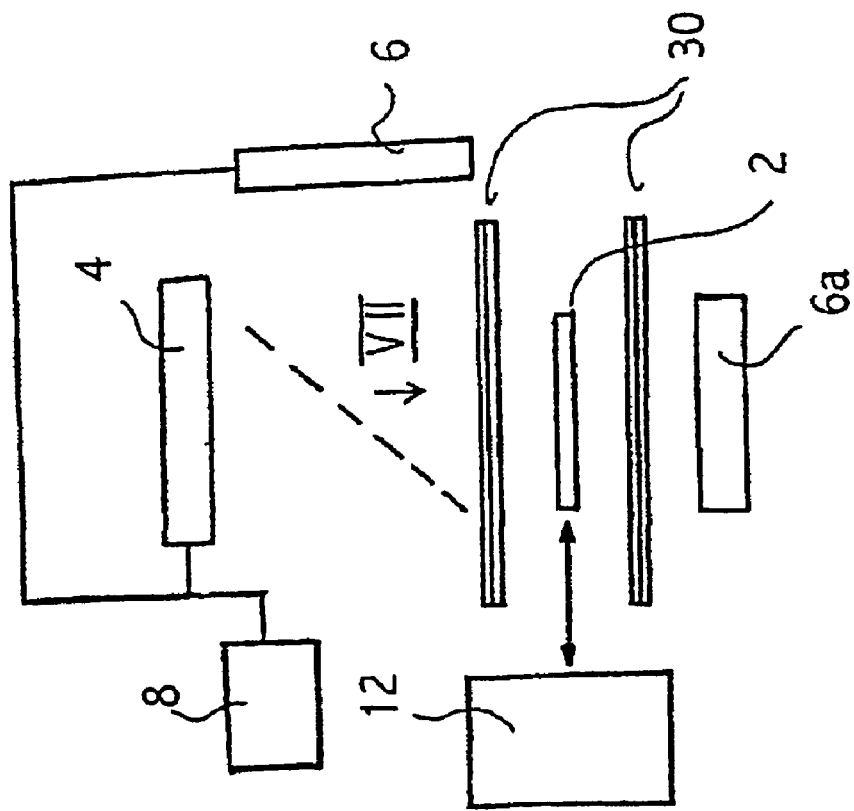
FIG. 6 shows in a block diagram a further variant of the apparatus according to the invention.

In the variant of the apparatus of FIG. 5, which is diagrammatically illustrated in FIG. 6, the device for immobilizing the beads has a coil pair 30, for example a Helmholtz coil pair, to generate a B field. One coil of the coil pair is located below the support body 2, whereas the other coil is positioned above the support 2. The coil pair 30 can be designed so as to generate an inhomogeneous B field in order to exert a directed force on the particles.

Figure 7:
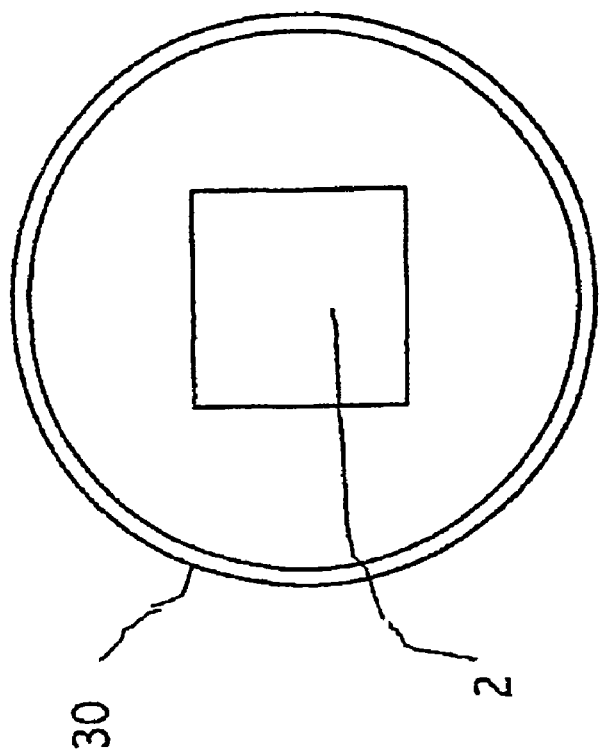
FIG. 7 shows a coil pair of FIG. 6, viewed in the direction indicated by the arrow VII in FIG. 6.

FIG. 7 shows a top view of the support body 2 and the coils 30, which indicates that the coils 30 do not shade the support body 2 in the light path. This also means that it is possible to carry out transmissive light observation of the support body 2 and of the particles to be provided therein or thereon by means of the detection matrix 6a.

In the previous exemplary embodiments, the microbeads were immobilized by means of magnetic, electric or electromagnetic fields. FIG. 8 illustrates another possibility of immobilizing microbeads in a microchannel 40 of the support body 2. FIG. 8 shows a section of a longitudinal section through a fluid channel 40 which is divided by an intermediate wall 52 into a main flow channel 40a and a low pressure channel 40b. The intermediate wall 52 has a multiplicity of micropores 54 which connect the main flow channel 40a with the low pressure channel 40b. The low pressure channel 40b is connected to a pump generating a low pressure compared to the pressure in the main flow channel 40a. In the arrangement according to FIG. 8, the microbeads 46 in the main flow channel 40a are immobilized on the intermediate wall 52, owing to the pressure conditions set. The diameter of the micropores 54 may be very much smaller than the diameter of the microbeads, as indicated in FIG. 8.

FIG. 9 shows a diagrammatic top view of a region of the intermediate wall 52 in FIG. 8. FIG. 9 indicates that the pores 54 are intended to be in an ordered pattern so that the immobilized beads 46 can be arranged in a corresponding pattern.

Alternatively, a random or chance distribution of the pores at high pore density may be provided for in an intermediate wall 52, as indicated in a view in FIG. 10, which corresponds to the perspective according to FIG. 9. In this context, the intermediate wall 52 may consist of an intrinsically porous material.

The detailed illustration of an intermediate wall in FIG. 11 indicates that in a possible variant the diameter of the pores 54 is only slightly smaller than the diameter of the microbeads 46.

FIG. 12 shows another possibility of immobilizing microbeads 46 on a support body 2. FIG. 12 shows a section of a longitudinal section through a fluidic channel 40 of the support body 2 observed here. The fluidic channel 40 is provided with an intermediate wall 52a which divides the fluidic channel into an upper main flow channel 40a and a lower low pressure channel 40b. The prevailing pressure in the low pressure channel 40b is lower than in the main flow channel 40a.

The intermediate wall 52a has, between microcolumns 56 made of silicon, Foturan or plastic, etc., depressions 58 whose bases contain 60 micropores or consist of intrinsically porous material. The micropores in the bases 60 permit fluidic flow from the main flow channel 40a to the low pressure channel 40b with corresponding decrease in pressure. This is accompanied by microbeads 46 supplied in a suspension attaching in the depressions 58.

As the fractional top view of the intermediate wall 52a according to FIG. 13 indicates, the depressions 58 and columns 56 are arranged in the example case according to a checkered pattern type.

FIG. 14 illustrates that, alternatively, the depressions 58 can be designed so as to be able to receive in each case only one layer of microbeads 46.

It should be noted that in the embodiments according to FIGS. 8-14 it is possible to use in support a B field or/and an electric field to immobilize microbeads which have been magnetically or electrically prepared accordingly.

Furthermore, it should be noted that means for complete or local temperature control of the support by means of optical or electrical energy input may be provided for. Possible means are resistance heating elements which are microtechnically integrated into the support body and which enable location-specific temperature control.

Furthermore, it should generally be noted that it is possible to apply, in embodiments in which the beads are immobilized electrically, an electric field which completely pervades the support body 2 in question or location-specific electric fields, it being possible for the latter to be generated, for example, by individually addressed electrodes on a CMOS circuit and/or by means of transparent LCD electrodes.

Likewise, in the embodiments in which the beads are immobilized magnetically, it may be provided for a magnetic field which completely pervades the support body to be generated or, as an alternative, for local magnetic fields to be generated in a space-resolved manner by means of coils or permanent magnets, one possible example being microcoils integrated into the support body for generating local magnetic fields.

The beads may, where appropriate, be transparent or at least partly transparent.

The FIGS. 15-17 show magnified sections of top views of various variants of microfluidic channel design. The boundaries of the microchannels preferably have inert surfaces.

The invention claimed is:

1. A method for integrated synthesis and analyte determination on a support, comprising the following steps:
   a) providing a support body (2),
   b) conducting a liquid containing particles (46) into or onto the support body (2),
   c) permanently immobilizing the particles (46) on at least one inner or outer surface (45) of the support body (2),
   d) conducting a liquid which contains receptors or building blocks (A, B) for synthesizing polymeric receptors over the immobilized particles (46),
   e) coupling the receptors or receptor building blocks (A, B) location-specifically, time-specifically or both to the immobilized particles (46) at predetermined positions of the support body (2),
   f) repeating, where appropriate, (d) and (e), until the desired receptors have been synthesized on the immobilized particles (46) at predetermined positions of the support body,
   g) contacting the receptors with a sample containing the analyte to be determined, and
   h) determining the analyte via binding to the receptors which are coupled to the immobilized particles (46).

2. The method as claimed in claim 1, wherein permanent immobilizing comprises a covalent chemical bond.

3. The method as claimed in claim 1, wherein the analyte is removed from the support body after the determination.

4. The method as claimed in claim 1, comprising repeating (f) a plurality of times, and wherein said receptors are synthesized for a subsequent cycle on the basis of the information from a preceding cycle.

5. The method as claimed in claim 1, wherein the support body (2) has a multiplicity of channels (40).

6. A method for integrated synthesis and analyte determination on a support, comprising the following steps:
   a) providing an integrated apparatus which comprises a programmable light source matrix (4), a detector matrix (6), a support body (2) arranged between said light source matrix and said detector matrix, wherein said support body has at least some transparent regions, and a means for supplying fluid into the support body and for discharging fluid from the support body,
   b) conducting a liquid containing particles (46) into or onto the support body (2),
   c) permanently immobilizing the particles (46) on at least one inner or outer surface (45) of the support body (2) by a covalent chemical bond,
   d) conducting a liquid which contains receptors or building blocks (A, B) for synthesizing polymeric receptors over the immobilized particles (46)
   e) coupling the receptors or receptor building blocks (A, B) location-specifically, time-specifically or both to the immobilized particles (46) at predetermined positions of the support body (2),
   f) repeating, where appropriate, steps (d) and (e), until the desired receptors have been synthesized on the immobilized particles (46) at the predetermined positions of the support body,
   g) contacting the receptors with a sample containing the analyte to be determined, and
   h) determining the analyte via binding to the receptors which are coupled to the immobilized particles (46) wherein said synthesis of the desired receptors, said determining analytes or both are monitored and controlled in at least one position on the support.

* * * * *